(12) United States Patent
Hindupur et al.

(10) Patent No.: US 11,927,503 B2
(45) Date of Patent: Mar. 12, 2024

(54) METHOD FOR DETERMINING A WELD INTEGRITY TEST RESULT

(71) Applicant: Cytiva Sweden AB, Uppsala (SE)

(72) Inventors: Sameera Simha Hindupur, Karnataka (IN); Manoj Kumar Ramakrishna, Karnataka (IN); Andreas Castan, Uppsala (SE); Swapnil Puranik, Karnataka (IN); Klaus Gebauer, Uppsala (SE)

(73) Assignee: Cytiva Sweden AB, Uppsala (SE)

( * ) Notice: Subject to any disclaimer, the term of this patent is extended or adjusted under 35 U.S.C. 154(b) by 477 days.

(21) Appl. No.: 17/276,981

(22) PCT Filed: Sep. 9, 2019

(86) PCT No.: PCT/EP2019/073926
§ 371 (c)(1),
(2) Date: Mar. 17, 2021

(87) PCT Pub. No.: WO2020/058012
PCT Pub. Date: Mar. 26, 2020

(65) Prior Publication Data
US 2022/0034748 A1 Feb. 3, 2022

(30) Foreign Application Priority Data

Sep. 21, 2018 (IN) .............................. 201841035641

(51) Int. Cl.
*G01M 3/28* (2006.01)
*B29C 65/00* (2006.01)
(Continued)

(52) U.S. Cl.
CPC ....... *G01M 3/2884* (2013.01); *B29C 65/8246* (2013.01); *B29C 66/522* (2013.01);
(Continued)

(58) Field of Classification Search
CPC ............. G01M 3/2884; B29C 65/8246; B29C 66/522; C12M 23/40; C12M 37/04; C12M 41/40
See application file for complete search history.

(56) References Cited

U.S. PATENT DOCUMENTS

2022/0023979 A1\* 1/2022 Klimas .................. G01N 29/46

FOREIGN PATENT DOCUMENTS

| EP | 3333560 A1 | 6/2018 |
| WO | 2016/078777 A1 | 5/2016 |
| WO | 2016/188781 A1 | 12/2016 |

OTHER PUBLICATIONS

PCT International Search Report and Written Opinion for PCT/EP2019/073926 dated Dec. 12, 2019 (8 pages).

\* cited by examiner

*Primary Examiner* — Eric S. McCall
(74) *Attorney, Agent, or Firm* — Eversheds Sutherland (US) LLP (57) ABSTRACT

The present invention relates to a computer implemented method for determining a weld integrity test result performed by a system configured to aseptically transferring cells to a container (BR), the method comprising welding (710) a vial to a connector to obtain a fluid-tight seal between the vial (V) and a connector (C), the connector being provided with a pair of conduits each having one end protruding through the connector and into the vial, sealing (720) an opposite end of one of the conduits, generating (730) a fluid pressure different to an ambient fluid pressure at an opposite end of the other conduit, measuring (740) a fluid pressure within at least one of the conduits, determining (750) a fluid pressure change based on the ambient (Continued)

pressure and the measured fluid pressure, determining (760) the weld integrity test result as pass or as fail based on the fluid pressure change.

9 Claims, 8 Drawing Sheets

(51) Int. Cl.
*B29C 65/82* (2006.01)
*C12M 1/00* (2006.01)
*C12M 1/12* (2006.01)
*C12M 1/34* (2006.01)

(52) U.S. Cl.
CPC ............ *C12M 23/40* (2013.01); *C12M 37/04* (2013.01); *C12M 41/40* (2013.01)

| Working Volume (ml) | Outer Diameter (mm) | Height (mm) of Product | Base | Cap |
|---|---|---|---|---|
| 1 | 12,5 | 48 | Conical Freestanding | Internal Thread |
| 2 | 12,5 | 48 | Round Non-Free standing | Internal Thread |
| 2 | 12,5 | 47 | Round Freestanding | Internal Thread |
| 2 | 12,5 | 47 | Round Freestanding | External Thread |
| 4 | 12,5 | 83 | Round Freestanding | External Thread |
| 5 | 12,5 | 86 | Round Non-Free standing | Internal Thread |
| 1 | 0 | 36,5 | Round Freestanding | External Thread |
| 1,6 | 0 | 47,7 | Round Freestanding | Internal Thread |
| 1,8 | 0 | 46,5 | Round Freestanding | External Thread |
| 4,5 | 0 | 90,5 | Round Freestanding | Internal Thread |
| 0,3 | 9 | 26 | Round Freestanding | Internal Thread |
| 0,21 | 9 | 26 | Round Freestanding | Internal Thread |
| 0,48 | 9 | 33,5 | Round Freestanding | Internal Thread |
| 0,53 | 9 | 33,5 | Round Freestanding | Internal Thread |
| 0,55 | 9 | 33,5 | Round Freestanding | Internal Thread |
| 0,58 | 9 | 33,5 | Round Freestanding | Internal Thread |
| 0,73 | 9 | 44 | Round Freestanding | Internal Thread |
| 0,78 | 9 | 44 | Round Freestanding | Internal Thread |
| 0,79 | 9 | 44 | Round Freestanding | Internal Thread |
| 0,8 | 9 | 44 | Round Freestanding | Internal Thread |
| 0,9 | 9 | 44 | Round Freestanding | Internal Thread |
| 1,15 | 9 | 51 | Round Freestanding | Internal Thread |
| 1,2 | 9 | 51 | Round Freestanding | Internal Thread |
| 1,01 | 9 | 51 | Round Freestanding | Internal Thread |
| 1,05 | 9 | 51 | Round Freestanding | Internal Thread |
| 0,5 | 8,8 | 35 | Self-Standing | Internal Thread |
| 1 | 8,8 | 48,5 | Self-Standing | Internal Thread |
| 1 | 12,5 | 41 | Self-Standing | External Thread |
| 1 | 12,4 | 30 | Non-Free Standing | External Thread |
| 1 | 12,4 | 41 | Self-Standing | External Thread |
| 1 | 12,5 | 42 | Self-Standing | Internal Thread |
| 1,8 | 12,5 | 48 | Self-Standing | External Thread |
| 1,8 | 12,4 | 44 | Self-Standing | External Thread |
| 1,8 | 12,4 | 48 | Self-Standing | External Thread |
| 1,8 | 12,5 | 49 | Self-Standing | Internal Thread |
| 1,8 | 12,5 | 48 | Non-Free Standing | Internal Thread |
| 3,6 | 12,5 | 72 | Self-Standing | Internal Thread |
| 3,6 | 12,5 | 70 | Non-Free Standing | Internal Thread |
| 4,5 | 12,5 | 91 | Self-Standing | External Thread |
| 4,5 | 12,5 | 92 | Self-Standing | Internal Thread |
| 4,5 | 12,5 | 92 | Non-Free Standing | Internal Thread |
| 2 | 0 | 0 | Non-Free Standing | External Thread |
| 1,2 | 0 | 0 | Self-Standing | External Thread |
| 2 | 12 | 47 | Self-Standing | External Thread |
| 4 | 0 | 0 | Self-Standing | External Thread |
| 5 | 0 | 0 | Self-Standing | External Thread |
| 1,2 | 0 | 0 | Self-Standing | Internal Thread |
| 2 | 10,5 | 48,7 | Self-Standing | Internal Thread |
| 2 | 0 | 0 | Non-Free Standing | Internal Thread |
| 4 | 0 | 0 | Non-Free Standing | Internal Thread |
| 5 | 0 | 0 | Non-Free Standing | Internal Thread |
| 5 | 0 | 0 | Self-Standing | Internal Thread |
| 1 | 11,7 | 38,1 | Self-Standing | External Thread |
| 1,2 | 12,7 | 38,1 | Self-Standing | External Thread |
| 1,5 | 11,7 | 47,5 | Self-Standing | External Thread |
| 2 | 12,7 | 47,5 | Self-Standing | External Thread |
| 5 | 11,7 | 88,9 | Self-Standing | External Thread |
| 15 | 33,3 | 46,0 | Self-Standing | External Thread |

Fig. 8

METHOD FOR DETERMINING A WELD INTEGRITY TEST RESULT

CROSS REFERENCE TO RELATED APPLICATIONS

This application claims the priority benefit of PCT/EP2019/073926, filed on Sep. 9, 2019, which claims the benefit of Indian Application No. 201841035641, filed on Sep. 21, 2018, the entire contents of which are incorporated by reference herein.

FIELD OF INVENTION

The present invention relates to a method for determining a weld integrity test result performed by a system configured to aseptically transferring cells to a container. In particular, a method for a system for aseptic transfer of cells from a transport container, such as a vial, to a bioreactor.

BACKGROUND OF THE INVENTION

Cell culture techniques have become vital to the study of animal cell structure, function and differentiation and for the production of many important biological materials, such as virus vaccines, enzymes, hormones, antibodies, interferon's, nucleic acids and virus vectors for gene therapy. Furthermore, cell culture and cell expansion is a very important step in cell therapy. For many cell culture approaches it is desired to expand a cell culture from a small cell population to a large cell population. For cell cultures it is conventional to grow the cells in a bioreactor, such as a shake-flask bioreactor or a disposable bioreactor, such as flexible bags made from dextran, cellulose or polyethylene based products.

In order to perform cell culture, it is necessary to have sterile cell culture materials. Conventional methods include sterilizing culture materials via autoclaving outside of the bioreactor or inside the bioreactor via steam sterilization. With the introduction of single use bioreactors, it may no longer possible to perform the sterilization via steam in the bioreactor. Therefore, it is necessary to provide pre-sterilized transport containers, e.g. vials, which allow cells to be introduced into the bioreactor aseptically without compromising the sterility.

US2014/0196791 describes a single use bioreactor comprising a micro carrier container and a bioreactor vessel, wherein the micro carriers are transferred to the vessel by gravity or flushing with a fluid. Transfer with gravity will not be complete, i.e. some of the micro carriers will stick to the walls of the container and not be transferred to the bioreactor vessel. To improve this, flushing of the container is suggested with for example cell cultivation medium.

In spite of the many bioreactors known in the art there is still a need of improved methods and systems for aseptic transfer of culture materials to bioreactors.

OBJECTS OF THE INVENTION

An objective of embodiments of the present invention is to provide a solution which mitigates or solves the drawbacks and problems described above.

SUMMARY OF THE INVENTION

The above objective is achieved by the subject matter described herein. Further advantageous implementation forms of the invention are further defined herein According to a first aspect of the invention, the above mentioned and other objectives are achieved by a computer implemented method for determining a weld integrity test result performed by a system configured to aseptically transferring cells to a container, the method comprising welding a vial to a connector to obtain a fluid-tight seal between the vial and a connector, the connector being provided with a pair of conduits each having one end protruding through the connector and into the vial, sealing an opposite end of one of the conduits, generating a fluid pressure different to an ambient fluid pressure at an opposite end of the other conduit, measuring a fluid pressure within at least one of the conduits, determining a fluid pressure change based on the ambient pressure and the measured fluid pressure, determining the weld integrity test result as pass or as fail based on the fluid pressure change.

An advantage of the embodiment according to the first aspect is that a pre-sterilized status can be maintained and/or any loss of fluid can be avoided.

According to a second aspect of the invention, the above mentioned and other objectives are achieved by a kit for aseptically transferring cells to a container, the kit comprising a connector made from thermoplastic, the connector being provided with a pair of conduits each having one end protruding through the connector and into the vial, at least one sealer coupled to an opposite end of one of the conduits and configured to either seal the opposite end of one of the conduits or to connect the opposite end of one of the conduits to a container.

According to a third aspect of the invention, the above mentioned and other objectives are achieved by a system configured to aseptically transferring cells to a container, the system comprising a vial made from thermoplastic and configured to hold the cells, a kit according to the second aspect of the invention, a pressure source coupled to the opposite end of the other conduit and configured to generate a fluid pressure different to an ambient fluid pressure at an opposite end of the other conduit, a welding arrangement configured to weld the vial to the connector to obtain an fluid-tight seal between the vial and the connector, and a control unit configured to control the welding arrangement to weld the vial to the connector, control the pressure source to generate a fluid pressure different to the ambient fluid pressure at an opposite end of the other conduit, receive a measured fluid pressure within at least one of the conduits, determine a fluid pressure change based on the ambient pressure and the measured fluid pressure, determine a weld integrity test result as pass or as fail based on the fluid pressure change.

The advantages of the second and third aspects are at least the same as for the first aspect.

Further applications and advantages of embodiments of the invention will be apparent from the following detailed description.

BRIEF DESCRIPTION OF THE DRAWINGS

FIG. 8 shows examples of dimensions of elongated vials.

A more complete understanding of embodiments of the invention will be afforded to those skilled in the art, as well as a realization of additional advantages thereof, by a consideration of the following detailed description of one or more embodiments. It should be appreciated that like reference numerals are used to identify like elements illustrated in one or more of the figures.

DETAILED DESCRIPTION

An "or" in this description and the corresponding claims is to be understood as a mathematical OR which covers "and" and "or", and is not to be understand as an XOR (exclusive OR). The indefinite article "a" in this disclosure and claims is not limited to "one" and can also be understood as "one or more", i.e., plural.

The term "vial" is used interchangeably with the term "transport container" herein and signifies any container, holder, repository, vessel suitable for aseptically transporting cells. The vial is typically sealed after cells are inserted into the vial before transportation. The vial typically comprises a material suitable for welding, such as thermoplastic. The vial is typically provided with a tube member having a shape suitable to weld to a connector of a system 100 configured to aseptically transferring cells to a container. In one example, a vial is an elongated tube having sealed ends.

The term "weld integrity test result" signifies a test result at least indicating a positive result if a fluid-tight seal between the vial and the connector has been achieved and a negative result if a fluid-tight seal between the vial and the connector has not been achieved. The "weld integrity test result" may further comprise a measure indicative of to what degree a fluid-tight seal between the vial and the connector has been achieved and/or a confidence measure indicating a confidence of the weld integrity test result.

The term "ambient fluid pressure" signifies ambient air pressure of the physical location of the system 100, e.g. the ambient air pressure of the room in where the system 100 is located.

Figure 1:
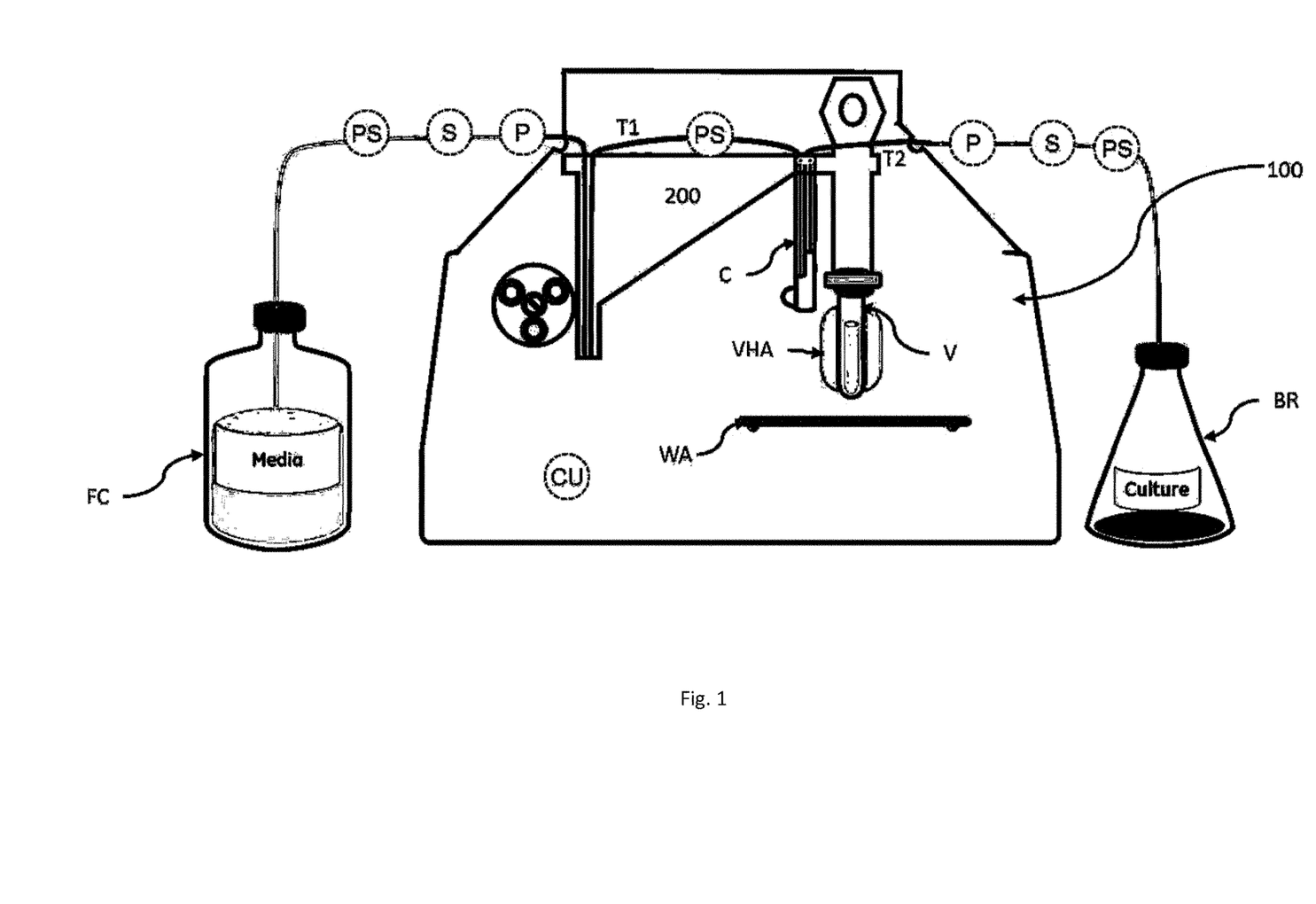
FIG. 1 shows a system configured to aseptically transfer cells to a container according to one or more embodiments of the present disclosure.

FIG. 1 shows a system 100 configured to aseptically transfer cells to a container according to one or more embodiments of the present disclosure. The system is configured to be coupled to one or more containers FC, BR, such as a buffer fluid container FC and/or a bioreactor BR.

In one embodiment, the system comprises a vial V, a pressure source PS, a welding arrangement WA and a control unit CU. The vial V may e.g. be made from thermoplastic and be configured to hold the cells. The pressure source PS may be coupled to the opposite end of one of the conduits and configured to generate a fluid pressure different to an ambient fluid pressure. The welding arrangement WA is configured to weld the vial to the connector to obtain a fluid tight seal between the vial V and the connector C. The control unit CU comprises processing circuitry and a memory, where the memory comprises instructions that when executed causes the processing circuitry of the control unit CU to perform any of the method steps described herein. The pressure source PS may be positioned anywhere between the one or more containers FC, BR. The pressure sensor P may be of an in-line type, configured to measure pressure of fluid passing through the pressure sensor P. The pressure sensor P may optionally or additionally be of non-intrusive type, e.g. measuring variation of the dimension of the conduit due to the pressure within at least one of the conduits.

The system 100 may optionally further comprise a vial heating arrangement VHA, communicatively coupled to the control unit and configured to heat the vial in response to a control signal from the control unit CU. In one example, the cells are frozen during transport and are later heated by the VHA before transfer of the cells to the container BR.

Figure 4:
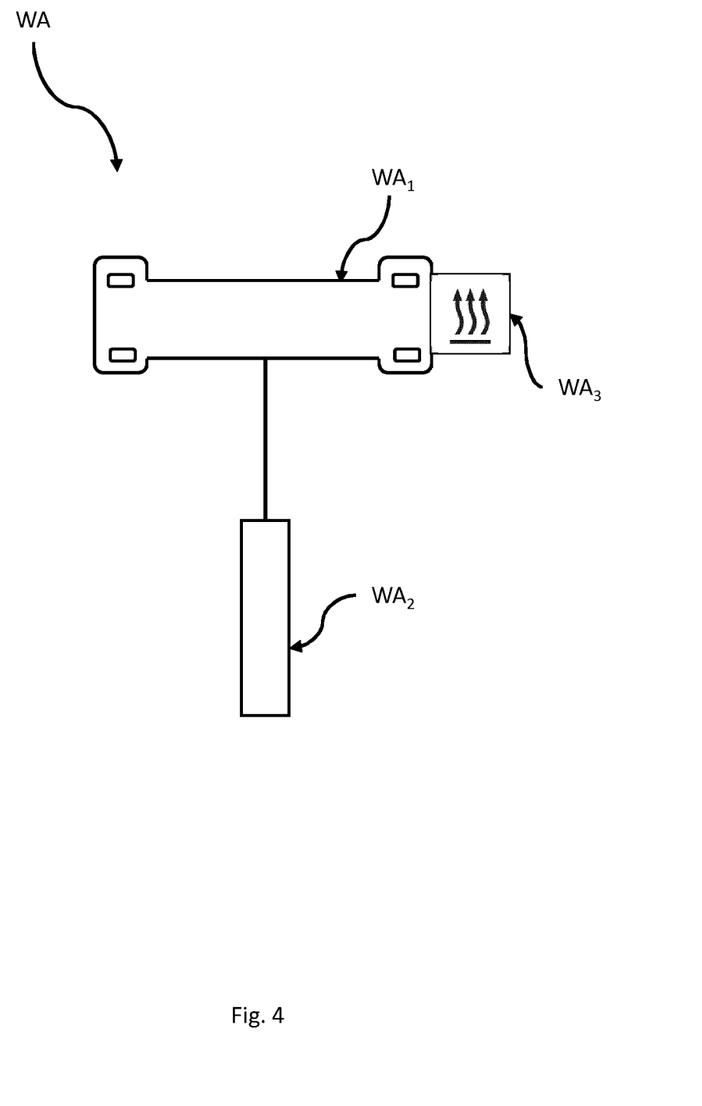
FIG. 4 shows a welding arrangement according to one or more embodiments of the present disclosure.

The welding arrangement WA is further described in relation to FIG. 4. The control unit CU is further described in relation to FIG. 6. A more detailed description of the system 100 is provided in relation to FIG. 5A and FIG. 5B.

In one example, a fluid comprised in a buffer fluid container FC is pumped into the vial V, and a mixture of cells and buffer fluid is transferred to the container/bioreactor BR, e.g. in the form of a shake-flask.

Figure 2:
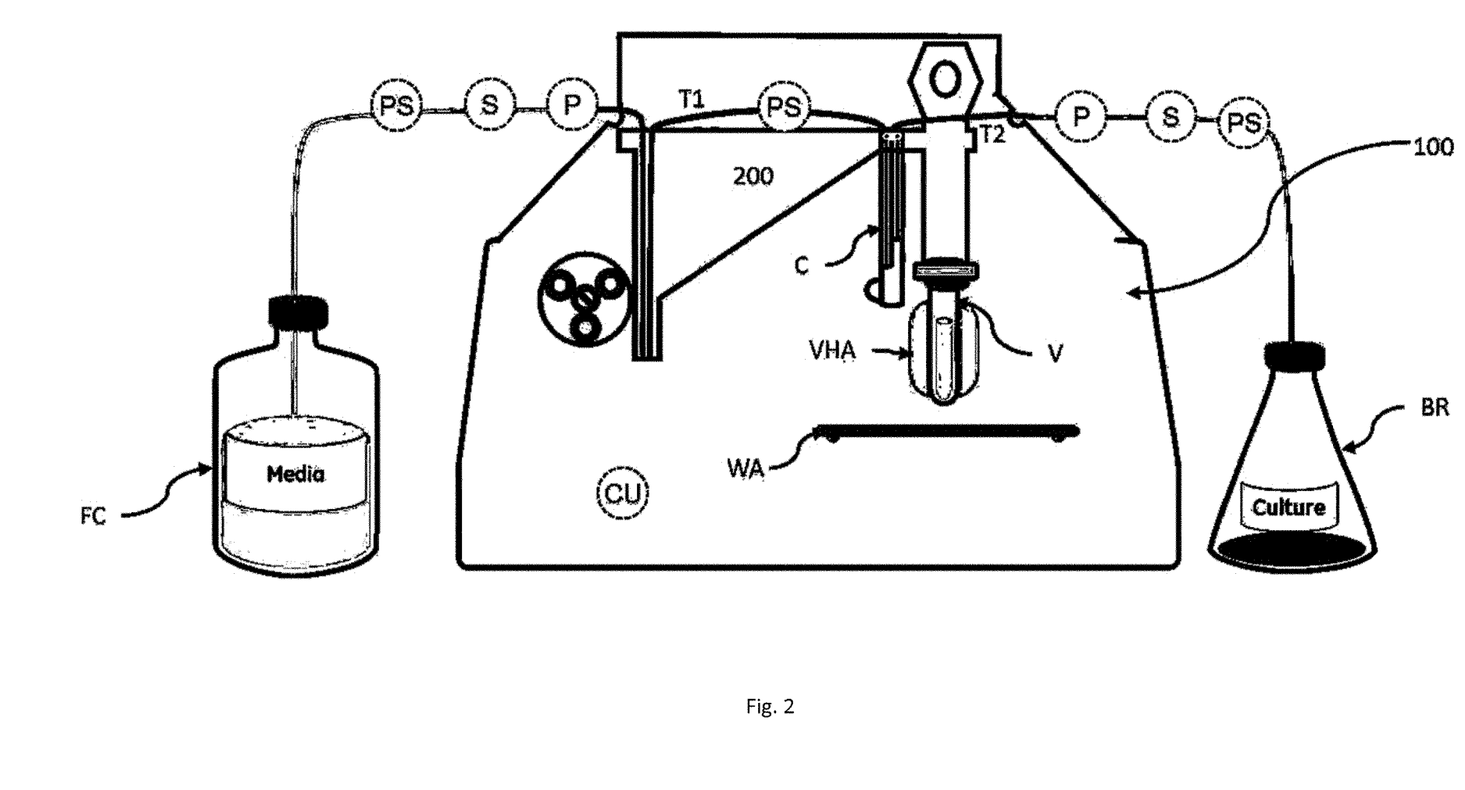
FIG. 2 illustrates the system after a vial and a connector have been welded together to obtain a fluid-tight seal between the vial and the connector.

FIG. 2 illustrates the system 100 after a vial V and a connector C have been welded together to obtain a fluid-tight seal between the vial and the connector. Thereby the system 100 can aseptically transfer cells to the bioreactor BR. In other words, the connector C the vial V form a single unit by welding a fluid-tight seal between the vial and the connector.

Figure 3:
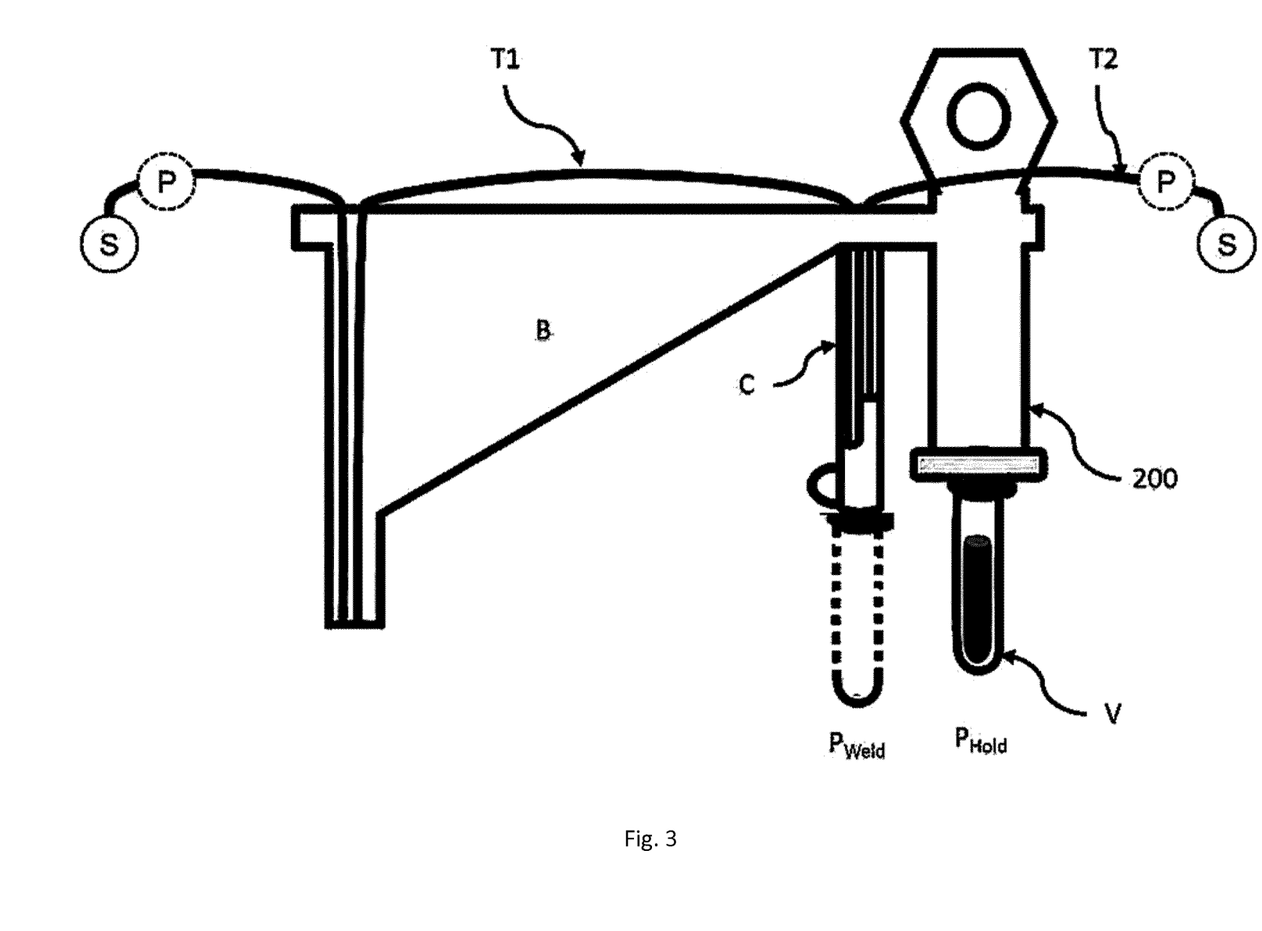
FIG. 3 shows a kit according to one or more embodiments of the present disclosure.

FIG. 3 shows a kit 200 according to one or more embodiments of the present disclosure.

In one embodiment, the kit comprises a connector C made from thermoplastic, the connector C being provided with a pair of conduits T1, T2 each having one end protruding through the connector C and into the vial V. The thermoplastic may be any suitable thermoplastic, such as polypropylene. The conduits may be comprised of any suitable material and have a hollow shape, allowing fluid to flow through the conduits. In one example, the conduits comprise plastic tubing. In one embodiment, the kit 200 is pre-sterilized. In one embodiment, the kit 200 is a disposable kit.

In one embodiment, the kit 200 further comprises at least one sealer S coupled to an opposite end of one of the conduits T1, T2 and configured to either seal the opposite end of one of the conduits T1, T2 or to couple or connect the opposite end of one of the conduits T1, T2 to a container, such as a buffer fluid container FC and/or a bioreactor BR. In other words, to either allow fluid to flow to/from the container FC/BR or to prevent fluid to flow to/from the container FC/BR. The at least one sealer S may be positioned at one end or both ends of the conduits T1, T2. In one embodiment, the at least one sealer S comprises an aseptic connector or a weld. In one embodiment, the sealer S comprises an electrically controllable valve communicatively coupled to the control unit CU, wherein the control unit is further configured control the valve to seal the opposite end of one or more of the conduits or to connect the opposite end of one of the conduits T1, T2 to a container, such as a buffer fluid container FC and/or a bioreactor BR.

Placing the sealer at the opposite end of one or both of the conduits T1, T2, has the advantage that the pre-sterilized status of the kit 200 can be maintained and/or any loss of fluid, either from the buffer fluid container FC and/or the bioreactor BR, can be avoided.

FIG. 3 further shows the kit 200 holding a vial V. The vial is shown when initially held by the kit 200 in a holding position $P_{Hold}$. An actuator AA (not shown) is then configured to move the vial V to a welding position $P_{Weld}$ before initiating the welding operation. The actuator is communicatively coupled and controlled by the control unit CU.

In one embodiment, the kit 200 further comprises a body B configured to hold the connector C and conduits T1, T2. Optionally the body is further configured to hold the vial V in the holding position $P_{Hold}$.

In one embodiment, the kit 200 further comprises a pressure sensor P configured to measure a fluid pressure within at least one of the conduits T1, T2. The pressure sensor P may be of an in-line type, configured to measure pressure of fluid passing through the pressure sensor P. The pressure sensor P may optionally or additionally be of non-intrusive type, e.g. measuring variation of the dimension of the conduit due to the pressure within at least one of the conduits.

In one embodiment, the kit 200 is configured for aseptically transferring cells to a container. In one embodiment, the kit 200 is a disposable kit.

FIG. 4 shows a welding arrangement WA according to one or more embodiments of the present disclosure. The welding arrangement WA is configured to weld the vial V to the connector C to obtain a fluid tight seal between the vial V and the connector C. Welding is performed when the vial V is held in the welding position $P_{Weld}$, typically by the actuator AA (not shown). The welding arrangement WA comprises a blade $WA_1$, an actuator $WA_2$ and a heater $WA_3$. The actuator $WA_2$ is attached to the blade $WA_1$ and is configured to move the blade between a resting position and an operational position. The heater $WA_3$ is configured to be in thermal contact with the blade $WA_1$ and to heat the blade $WA_1$ in response to a control signal received from the control unit CU. The actuator $WA_2$ and heater $WA_3$ are both communicatively coupled to and controlled by the control unit CU.

In one example, the vial V is held in the welding position $P_{Weld}$, aligned with the connector C such that the surface of the vial facing upwards towards the connector C is completely covered by a surface of the connector C facing downwards. The arrangement WA then positions the blade $WA_1$ in the operational position between the upwards and downward facing surfaces, where the blade $WA_1$ is heated by the heater $WA_3$ to a melting temperature of the thermoplastic. Examples of such temperatures are 378, 380 and 381 degrees Celsius. The welding arrangement WA then positions the blade $WA_1$ at the resting position where the blade $WA_1$ no longer is in contact with either the vial V or the connector C. The vial V and the connector C are then held or pressed together by the actuator AA (not shown) until the thermoplastic cools down and sets. A weld integrity test result can then be determined to determine if the weld between the vial V and the connector C is fluid-tight.

Figure 5A:
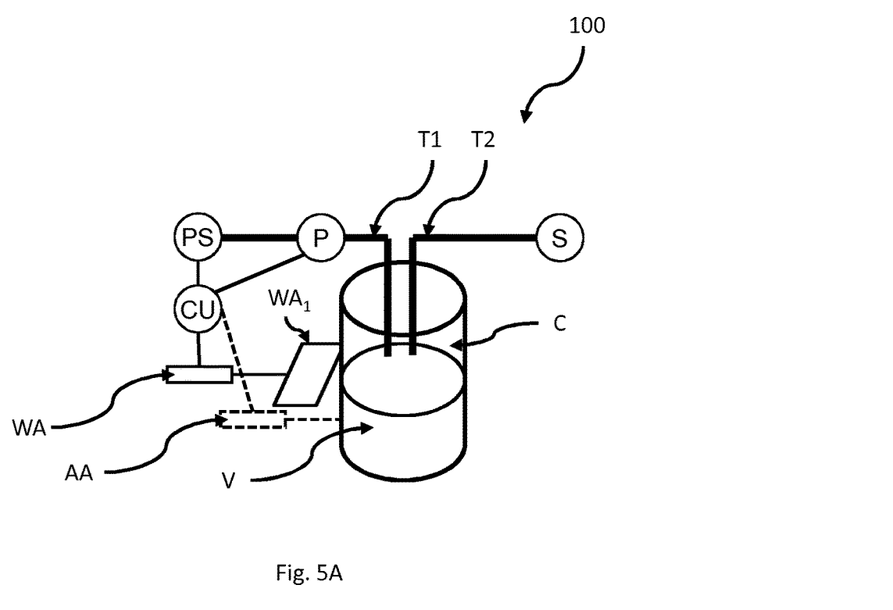
FIG. 5A shows details of the system according to one or more embodiments of the present disclosure.

FIG. 5A shows details of the system 100 according to one or more embodiments of the present disclosure.

FIG. 5A shows how the system 100 comprises the vial V, the connector C, the connector C being provided with a pair of conduits T1, T2 each having one end protruding through the connector C and into the vial V.

The system may further comprise the at least one sealer S coupled to an opposite end of one of the conduits T1, T2 and configured to either seal the opposite end of one of the conduits T1, T2 or to connect the opposite end of one of the conduits T1, T2 to a container, such as a buffer fluid container FC and/or a bioreactor BR. The at least one sealer S may be positioned at one end or both ends of one of the conduits T1, T2.

The connector C may be comprised in the kit 200, as further described in relation to FIG. 3.

The system may further comprise the pressure source PS coupled to, e.g. the opposite end of T1, the other conduit and configured to generate a fluid pressure different to an ambient fluid pressure at an opposite end of the other conduit.

The system may further comprise the welding arrangement WA configured to weld the vial to the connector to obtain a fluid tight seal between the vial V and the connector C using the heated blade $WA_1$.

The system may further comprise the actuator AA configured to move the vial V between the holding position $P_{Hold}$ and the welding position $P_{Weld}$ in response to a control signal received from the control unit CU. In other words, the actuator is communicatively coupled and controlled by the control unit CU.

The system may further comprise the control unit CU, which is communicatively coupled to a selection of any of the pressure source PS and/or the pressure sensor P and/or the welding arrangement WA and/or the actuator AA. Optionally, the control unit CU may be communicatively coupled to the at least one sealer S (not shown), e.g. when the sealer S comprises a controllable valve.

The system may further comprise the pressure sensor P configured to measure pressure within at least one conduit of the conduits T1, T2. In one embodiment, the pressure sensor P is configured to measure pressure within a first conduit T1 of the conduits and/or measure pressure within a second conduit T2 of the conduits T1, T2.

In FIG. 5A an example is shown where the pressure sensor P is configured to measure pressure within a first conduit T1 of the conduits, where the first conduit T1 is also coupled to the pressure source PS. In other words, the pressure sensor measures pressure within the conduit configured to be coupled to the buffer fluid container FC.

Figure 5B:
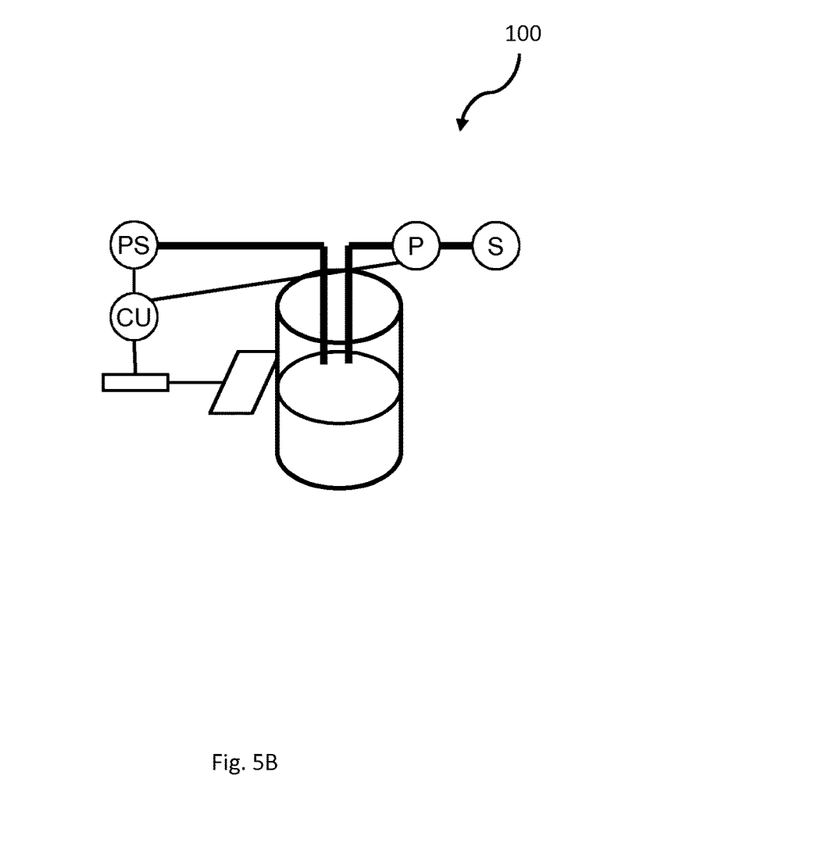
FIG. 5B shows an alternative arrangement of a pressure sensor according to one or more embodiments of the present disclosure.

FIG. 5B shows an alternative arrangement of a pressure sensor according to one or more embodiments of the present disclosure. In FIG. 5B an example is shown where the pressure sensor P is configured to measure pressure within a second conduit T2 of the conduits T1, T2, where the second conduit T2 is further coupled to the at least one sealer S. In other words, the pressure sensor measures pressure within the conduit configured to be coupled to the bioreactor BR.

Figure 6:
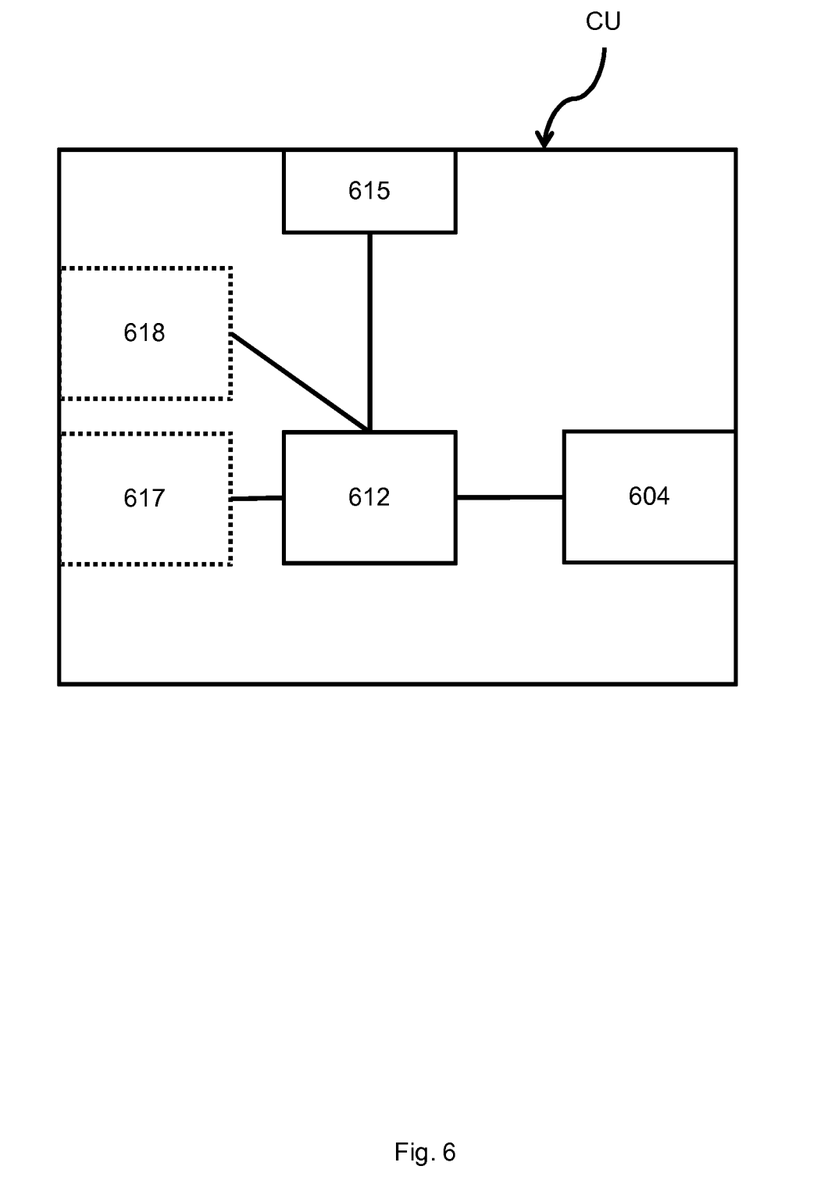
FIG. 6 shows the control unit according to one or more embodiments of the present disclosure.

FIG. 6 shows the control unit CU according to one or more embodiments of the present disclosure. The control unit CU may be in the form of e.g. an Electronic Control unit, a server, an on-board control unit, a stationary computing device, a laptop control unit, a tablet control unit, a handheld control unit, a wrist-worn control unit, a smart watch, a smartphone or a smart TV. The control unit CU may comprise processing circuitry 612 communicatively coupled to a transceiver 604 configured for wired or wireless communication. The control unit CU may further comprise at least one optional antenna (not shown in figure). The antenna may be coupled to the transceiver 604 and is configured to transmit and/or emit and/or receive wired or wireless signals in a communication network, such as WiFi, Bluetooth, 3G, 4G, 5G etc. In one example, the processing circuitry 612 may be any of a selection of a processor and/or a central processing unit and/or processor modules and/or multiple processors configured to cooperate with each-other. Further, the control unit CU may further comprise a memory 615 communicatively coupled to the processing circuitry 612. The memory 615 may e.g. comprise a selection of a hard RAM, disk drive, a floppy disk drive, a flash drive or other removable or fixed media drive or any other suitable memory known in the art. The memory 615 may contain instructions executable by the processing circuitry to perform any of the steps or methods described herein. The processing circuitry 612 may be communicatively coupled to a selection of any of the transceiver 604 and the memory 615. The control unit CU may be configured to send/receive control signals directly to any of the above mentioned units or to external nodes or to send/receive control signals via a wired and/or wireless communications network.

The wired/wireless transceiver 604 and/or a wired/wireless communications network adapter may be configured to send and/or receive data values or parameters as a signal to or from the processing circuitry 612 to or from other external nodes.

In an embodiment, the transceiver 604 communicates directly to external nodes or via the wireless communications network.

In one or more embodiments the control unit CU may further comprise an input device 617, configured to receive input or indications from a user and send a user input signal indicative of the user input or indications to the processing circuitry 612.

In one or more embodiments the control unit CU may further comprise a display 618 configured to receive a display signal indicative of rendered objects, such as text or graphical user input objects, from the processing circuitry 612 and to display the received signal as objects, such as text or graphical user input objects.

In one embodiment the display 618 is integrated with the user input device 617 and is configured to receive a display signal indicative of rendered objects, such as text or graphical user input objects, from the processing circuitry 612 and to display the received signal as objects, such as text or graphical user input objects, and/or configured to receive input or indications from a user and send a user-input signal indicative of the user input or indications to the processing circuitry 612.

In a further embodiment, the control unit CU may further comprise and/or be coupled to one or more additional sensors (not shown in the figure) configured to receive and/or obtain and/or measure physical properties pertaining to the system 100 and send one or more sensor signals indicative of the physical properties to the processing circuitry 612. An example of such an additional sensor may be an ambient air pressure sensor configured to measure the ambient air pressure where the system 100 is located.

In one or more embodiments, the processing circuitry 612 is further communicatively coupled to the input device 617 and/or the display 618 and/or the additional sensors.

In embodiments, the communications network communicate using wired or wireless communication techniques that may include at least one of a Local Area Network (LAN), Metropolitan Area Network (MAN), Global System for Mobile Network (GSM), Enhanced Data GSM Environment (EDGE), Universal Mobile Telecommunications System, Long term evolution, High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX) and ultrasonic communication, etc., but is not limited thereto.

Moreover, it is realized by the skilled person that the control unit CU may comprise the necessary communication capabilities in the form of e.g., functions, means, units, elements, etc., for performing the present solution. Examples of other such means, units, elements and functions are: processors, memory, buffers, control logic, encoders, decoders, rate matchers, de-rate matchers, mapping units, multipliers, decision units, selecting units, switches, interleavers, de-interleavers, modulators, demodulators, inputs, outputs, antennas, amplifiers, receiver units, transmitter units, DSPs, MSDs, TCM encoder, TCM decoder, power supply units, power feeders, communication interfaces, communication protocols, etc. which are suitably arranged together for performing the present solution.

Especially, the processing circuitry of the present disclosure may comprise one or more instances of a processor, processor modules and multiple processors configured to cooperate with each-other, Central Processing Unit (CPU), a processing unit, a processing circuit, a processor, an Application Specific Integrated Circuit (ASIC), a microprocessor, a Field-Programmable Gate Array (FPGA) or other processing logic that may interpret and execute instructions. The expression "processing circuitry" and/or "processing means" may thus represent a processing circuitry comprising a plurality of processing circuits, such as, e.g., any, some or all of the ones mentioned above. The processing means may further perform data processing functions for inputting, outputting, and processing of data comprising data buffering and device control functions, such as call processing control, user interface control, or the like.

Figure 7:
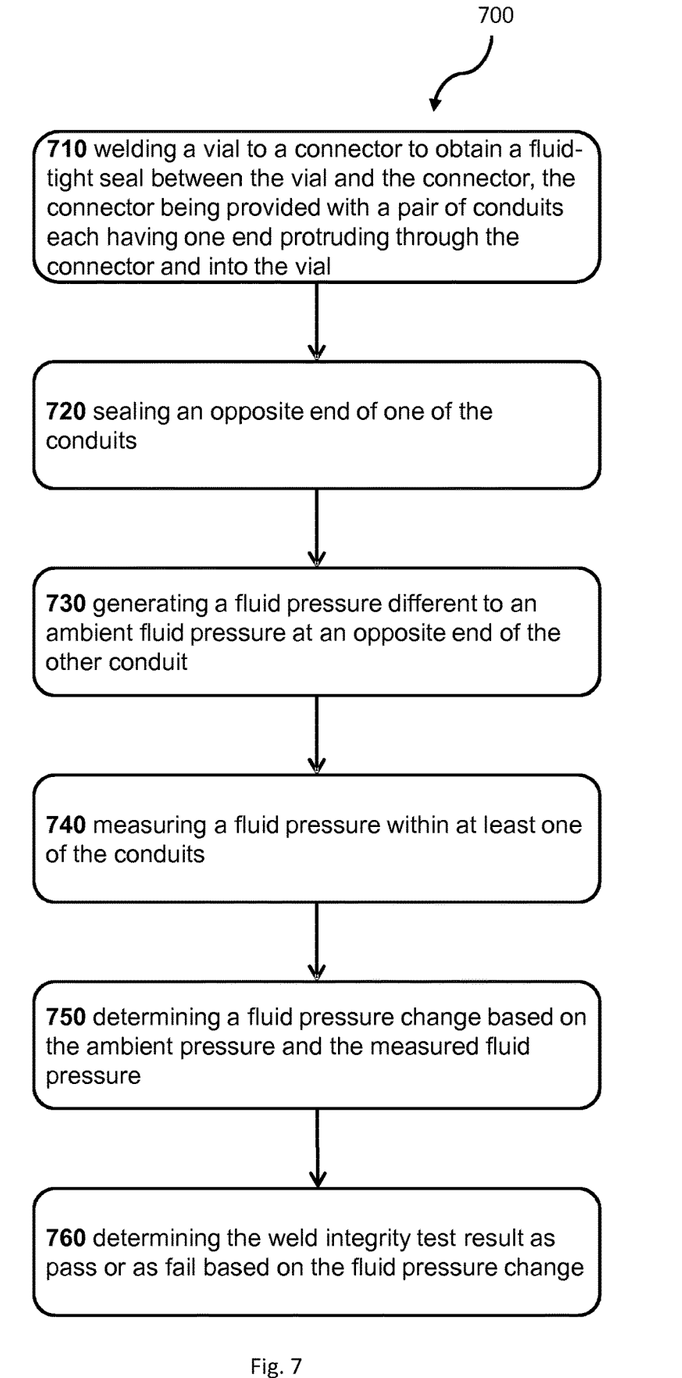
FIG. 7 shows a flowchart of a method according to one or more embodiments of the present disclosure.

FIG. 7 shows a flowchart of a method 700 according to one or more embodiments of the present disclosure. The method may be a computer implemented method for determining a weld integrity test result. The method 700 is performed by a system 100 configured to aseptically transferring cells to a container BR, the method comprising:

Step 710: welding a vial to a connector to obtain a fluid-tight seal between the vial V and the connector C, the connector being provided with a pair of conduits each having one end protruding through the connector and into the vial.

Welding is further described in relation to FIG. 4. The connector may or may not be comprised in a kit 200, as further described in relation to FIG. 3.

Step 720: sealing an opposite end of one of the conduits. The end may be sealed using the at least one sealer S, e.g. in the form of an aseptic connector or a weld, as further described in relation to FIG. 3.

Step 730: generating a fluid pressure different to an ambient fluid pressure at an opposite end of the other conduit. The fluid pressure is generated within one of the conduits. Generation of fluid pressure is further described in relation to FIG. 1, FIG. 5A and FIG. 5B. In one example, the ambient fluid pressure is the same as an ambient air pressure of the location of the system 100.

Step 740: measuring a fluid pressure within at least one of the conduits. The fluid pressure is typically obtained as measurement values from the pressure sensor P. The fluid pressure is measured within a first conduit T1 of the conduits and/or measure pressure within a second conduit T2 of the conduits T1, T2.

Step 750: determining a fluid pressure change based on the ambient pressure and the measured fluid pressure. In one embodiment, the fluid pressure change may be calculated as a difference between a predetermined or measured ambient pressure and the measured fluid pressure. In one embodiment, the fluid pressure change may be calculated as a difference between statistical measures of the ambient pressure and the fluid pressure, e.g. average, standard deviation etc. It is realized that any suitable statistical measure may be used to represent the fluid pressure change.

Step 760: determining the weld integrity test result as pass or as fail based on the fluid pressure change. In one embodiment, the weld integrity test result is determined as pass if the fluid pressure change is equal to or above a threshold or determining the test result as fail if the pressure is below the threshold. In one embodiment, the weld integrity test result is determined as pass if the fluid pressure change is equal to or below a threshold or determining the test result as fail if the pressure is above the threshold.

In one example, the ambient pressure is one (1) bar. The generated pressure is 2 bar and the threshold is set to 1.1 bar. If the measured pressured pressure is ≥1.1 bar the weld integrity test result is determined as a pass.

If the measured pressured pressure is <1.1 bar the weld integrity test result is determined as a fail.

In one further example, the ambient pressure is one (1) bar. The generated pressure is −2 bar and the threshold is set to −1.1 bar. If the measured pressured pressure is ≤−1.1 bar, the weld integrity test result is determined as a pass. If the measured pressured pressure is >−1.1 bar the weld integrity test result is determined as a fail.

In some situations, it is desirable to detect even smaller leaks in the weld

In one embodiment, the method further comprises:
sealing the opposite end of the other conduit,
halting the generation of the fluid pressure,
performing multiple fluid pressure measurements over a period of time,
determining a fluid pressure trend based on the multiple fluid pressure measurements, and,
determining the weld integrity test result as fail if the fluid pressure trend is indicative of increasing or decreasing measured fluid pressure.

In one embodiment, the fluid pressure is generated at a higher pressure which is greater than the ambient fluid pressure or the fluid pressure is generated at a lower pressure which is less than the ambient fluid pressure.

In some embodiments, the quality of the test result is further improved by first generating a pressure higher than ambient pressure and determining a partial result. Subsequently a pressure that is lower than ambient pressure is generating and a second partial result is determined. A final result can then be determined by combining both of the partial results. In one example, if both the partial results indicate a pass, then a final result of pass can be determined.

In one embodiment, the steps of generating 730 a fluid pressure, measuring 740 a fluid pressure and determining 750 a fluid pressure change are performed both for the higher pressure and for the lower pressure and wherein the weld integrity test result is based on the fluid pressure change resulting from generating both the higher pressure and from the lower pressure.

In one embodiment, the lower pressure comprises a vacuum pressure. In one embodiment the vacuum pressure comprises low and/or medium vacuum pressure. In the context of this disclosure, low vacuum is defined as the range [3-100 kPa] and medium vacuum is defined as the range [0.1 Pa-3 kPa].

FIG. 8 shows examples of dimensions of elongated vials. The table in FIG. 8 shows examples of elongated vial dimensions. The first column gives the volume or working volume of a vial, the second column specifies the outer dimensions/diameter of the vial, the third column specifies the length of the vial, the forth column specifies the shape of the base and the fifth column the cap.

Finally, it should be understood that the invention is not limited to the embodiments described above, but also relates to and incorporates all embodiments within the scope of the appended independent claims.

The invention claimed is:

1. A computer implemented method for determining a weld integrity test result performed by a system configured to aseptically transferring cells to a container, the method comprising:
    welding a vial to a connector to obtain a fluid-tight seal between the vial and a connector, the connector being provided with a pair of conduits each having one end protruding through the connector and into the vial,
    sealing an opposite end of one of the conduits,
    generating a fluid pressure different to an ambient fluid pressure at an opposite end of the other conduit,
    measuring a fluid pressure within at least one of the conduits,
    determining a fluid pressure change based on the ambient pressure and the measured fluid pressure, and
    determining the weld integrity test result as pass or as fail based on the fluid pressure change.

2. The method of claim 1, wherein the weld integrity test result is determined as pass if the fluid pressure change is equal to or above a threshold or determining the test result as fail if the pressure is below the threshold.

3. The method of claim 1, wherein the method further comprises:
    sealing the opposite end of the other conduit,
    halting the generation of the fluid pressure,
    performing multiple fluid pressure measurements over a period of time,
    determining a fluid pressure trend based on the multiple fluid pressure measurements, and,
    determining the weld integrity test result as fail if the fluid pressure trend is indicative of increasing or decreasing measured fluid pressure.

4. A control unit, wherein the control unit is configured to perform the method according to claim 1.

5. A computer program comprising computer-executable instructions for causing a control unit, when the computer-executable instructions are executed on a processing unit comprised in the control unit, to perform any of the method steps according to claim 1.

6. A carrier containing the computer program of claim 5, wherein the carrier is one of an electronic signal, optical signal, radio signal, or computer readable storage medium.

7. The method of claim 1, wherein
    the fluid pressure is generated at a higher pressure which is greater than the ambient fluid pressure, or
    the fluid pressure is generated at a lower pressure which is less than the ambient fluid pressure.

8. The method of claim 7, wherein the steps of generating a fluid pressure, measuring a fluid pressure and determining a fluid pressure change are performed both for the higher pressure and for the lower pressure, and wherein the weld integrity test result is based on the fluid pressure change resulting from generating both the higher pressure and from the lower pressure.

9. The method of claim 7, wherein the lower pressure comprises a vacuum pressure.

* * * * *